United States Patent [19]

Albrecht et al.

[11] 3,939,156

[45] Feb. 17, 1976

[54] CARDENOLIDES

[75] Inventors: Hans Peter Albrecht, Lutzelsachsen; Günter Neugebauer, Mannheim, both of Germany

[73] Assignee: Knoll A.G. Chemische Fabriken, Ludwigshafen (Rhine), Germany

[22] Filed: July 15, 1974

[21] Appl. No.: 488,421

[30] Foreign Application Priority Data
July 18, 1973 Germany.............................. 2336445

[52] U.S. Cl............................. 260/239.57; 424/241
[51] Int. Cl.²......................................... C07J 19/00

[58] Field of Search................................ 260/239.57

[56] References Cited
OTHER PUBLICATIONS
Merck Index, 8th Edition (1968) pp. 364–365.

*Primary Examiner*—Elbert L. Roberts
*Attorney, Agent, or Firm*—Curtis, Morris & Safford

[57] ABSTRACT

Novel cardenolides having desirable cardiac activity and which are readily reabsorbed internally, a process for their preparation and therapeutic compositions containing said cardenolides are disclosed.

36 Claims, No Drawings

CARDENOLIDES

The present invention relates to new cardio-active steroids and to a process for preparing such compounds.

Known cardio-active steroids are mainly glycosides. The aglycones of these compounds, as well as structurally similar steroids have hitherto been of little importance in the therapy of cardiac diseases, because they have only a short effective period.

It has now been found that certain 3-hydroxycardenolides may nevertheless be used to good effect because of their favorable action spectrum.

The compounds of the invention have the formula:

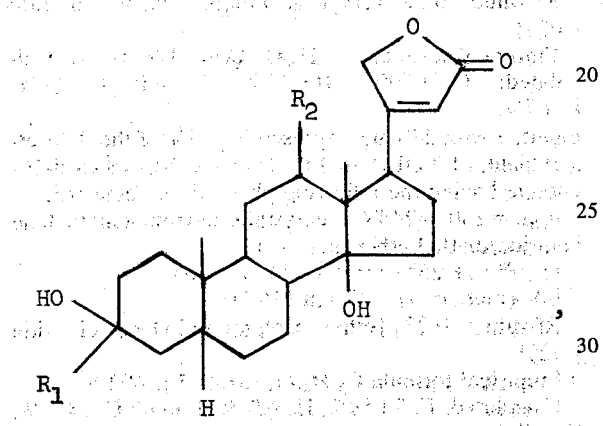

in which $R_1$ is alkyl of 1 to 4 carbon atoms, vicinal epoxy-or dihydroxyalkyl of 2 to 4 carbon atoms, alkenyl or alkinyl of 2 to 4 carbon atoms, or phenyl and $R_2$ is H or OH.

Compounds in which $R_1$ is methyl, ethyl, oxiranyl, 2',3'-epoxypropyl, 1',2'-dihydroxyethyl, 2',3'-dihydroxypropyl, vinyl, allyl, ethinyl or phenyl are preferred.

Furthermore, the present invention also relates to therapeutic compositions comprising such compounds in association with a therapeutically acceptable carrier. The invention also relates to a process for producing the compounds defined above by reacting the corresponding 3-oxocardenolide of the formula:

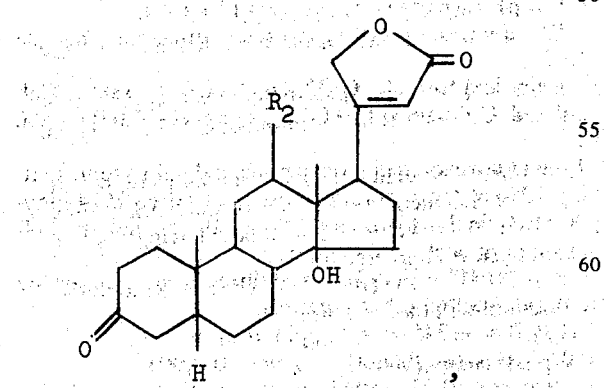

in which $R_2$ is H or OH with an organo-metallic compound of the formula
$R_3 — Me$ or $R_3 — MgX$, in which $R_3$ represents a saturated or unsaturated hydrocarbon residue of from 1 to 4 carbon atoms, or phenyl, Me represents lithium, sodium or potassium and X represents chlorine, bromine or iodine. If $R_3$ represents an unsaturated alkenyl group, the double bond can then be, and preferably is, hydroxylated or epoxylated.

The reaction of the 3-oxocardenolide with the organometallic compound is carried out in an inert solvent, such as, for example, tetrahydrofuran. It is advantageous to use an excess of the organo-metallic compound because the free hydroxy groups on the steroid react with the organo-metallic compound to form salts. The organo-metallic compound is preferably used in a 2 to 6-fold excess. When using compounds of the formula $R_3 — Me$, the reaction is carried out in the absence of atmospheric oxygen. When Grignard reagents are used, it is preferable to exclude atmospheric oxygen. The 3-oxocardenolides are generally reacted with the organo-metallic compound at a temperature of between $-70°C$ and $+20°C$ for a reaction period of between about 4 and 24 hours.

Although the preparation of tertiary alcohols by the addition of alkyl-metal or aryl-metal compounds to ketones and esters is generally known, see, for example L. F. Fieser and M. Fieser, Organ. Chemie, page 318 et seq., Verlag Chemie Weinheim 1968, it is surprising that this reaction is successful in selectively effecting this addition reaction on 3-oxocardenolides so that only the 3-ketocarbonyl group reacts; the carbonyl group on the unsaturated lactone ring, which in fact is an ester carbonyl group, is not attacked.

Double bonds in the substituents on the 3-position of the cardenolide may be hydroxylated or epoxylated if the reaction conditions are maintained substantially neutral, i.e. at a pH between about 6 and 8. If the reaction conditions are strongly acid or alkaline, secondary reactions occur. For hydroxylation, the method of Plaha et al. (Coll. Czech. Chem. Comm. 25, 237 (1960)) has proved particularly useful. This method is carried out using osmium tetroxide, barium chlorate in aqueous tetrahydrofuran. The epoxylation is particularly successful with the use of hydrogen peroxide/acetonitrile in methanol in the presence of potassium hydrogen carbonate (see G. B. Payne et al., J. Org. Chem. 26, 651, 659 (1961)).

As can be seen from tests performed on guinea-pigs and cats the new compounds, more particularly the 3β-hydroxy compounds, have a good cardiac action in mammals and are easily reabsorbed internally. The onset of the effect of these compounds is more rapid than that of known steroids at present being used. Moreover, the compounds of the present invention have a wider range of therapeutic use and act more strongly. For these reasons the new compounds are very suitable for the treatment of decompensated and compensated cardiac insufficiency and of senile heart conditions. The new compounds shall be administered orally as tablets or solutions in a dosage range between 0.01 and 0.2 mg/kg body weight. Tablets shall contain between 0.1 and 0.5 mg of active compound.

The invention will be further described, by way of example only, with reference to following examples. All of the Rf values quoted in these examples have been ascertained using kieselgel plates (kieselgel F) manufactured by E. Merck of Darmstadt, and all thin layer chromatograms were carried out using these plates.

EXAMPLE 1

A solution of methyl lithium (34 ml; 68 mMol) in ether is added to a solution of digitoxigenone (5.0 g; 13.4 mMol) in absolute tetrahydrofuran (250 ml) at a temperature of between −60° and −70°C. while stirring slowly under an inert gas atmosphere. The reaction mixture is stirred for four hours at −60°C., the temperature then being allowed to rise to room temperature during the course of thirty minutes. The reaction is then terminated by the addition of a saturated aqueous ammonium chloride solution (70 ml). After the addition of chloroform (1000 ml) thereto, the organic phase is washed with saturated aqueous sodium bicarbonate solution and with water, dried over sodium sulfate and evaporated.

The crude product (5.45 g) is separated by chromatography on a kieselgel column using methylene chloride/acetone (10/1) as eluant. The separation is followed by thin layer chromatographic analysis of the individual fractions, the chromatographically identical fractions being combined and evaporated. There are obtained, in order of rising polarity, firstly 0.2 g of unconverted digitoxigenone. Further elution followed by crystallization of the corresponding fractions then yields 2.88 g (55% of the theoretical yield) of 3β,14-dihydroxy-3-methyl-5β,14β-card-20-enolide, which has the following physical characteristics:

m.p. = 254° − 262°C. (recrystallized from a methylene chloride/diethyl ether mixture),
$[\alpha]_D^{20} = +25.9°$ ($c = 0.5$, chloroform),
UV peak (methanol): 217 nm (16 800)
Rf-value: 0.31 [ethyl acetate/methylene chloride (3/2)], and an empirical formula of $C_{24}H_{36}O_4$ (Mol. Wt. 388.5):

Calculated: C, 74.19%; H 9.34%.
Found : C, 74.3%; H, 9.4%.

and 0.95g (18% of the theoretical yield) of 3α,14-dihydroxy-3-methyl-5β,14β-card-20-enolide having the following physical characteristics:- m.p. = 212° − 222°C. (recrystallized from a methylene chloride/diethyl ether mixture),
$[\alpha]_D^{20} = +24.6°$ ($c = 0.46$, chloroform)
UV peak (methanol); 217 nm (17 000)
Rf-value: 0.17 [ethyl acetate/methylene chloride (3/2)] and an empirical formula of $C_{24}H_{36}O_4$ (Mol. Wt. 388.5): Calculated: C, 74.19 %; H, 9.34 %. Found: C, 74.1 %; H, 9.3 %.

EXAMPLE 2

53.6 ml (53.6 mMol) of a solution of methylmagnesium iodide in iso-amyl ether are added to a stirred solution of digitoxigenone (5.0 g, 13.4 mMol) in absolute tetrahydrofuran (250 ml) at −60°C in an inert gas atmosphere. The reaction mixture is stirred for six hours at −60°C and subsequently worked up in a manner analogous to that described in Example 1 and purified. There are thus obtained 2.2 g (42 % of the theoretical yield) of 3β,14-dihydroxy-3-methyl-5β,14β-card-20-enolide and 0.9 g (17 % of the theoretical yield) of 3β,14-dihydroxy-3-methyl-5β,14β-card-20-enolide. The physical characteristics of these compounds are given in Example 1.

EXAMPLE 3

Digitoxigenone (1.86 g, 5 mMol) is reacted in a manner analogous to that described in Example 1 with 25 ml (25 mMol) of a suspension of ethyl lithium in benzene. The crude product (2.3 g) is subjected to chromatography on kieselgel. By using a 40:1 mixture of methylene chloride and methanol as eluant, there is obtained 0.3 g of unreacted digitoxigenone and 1.1 g of a mixture of the two isomers of 3-ethyl-3,14-dihydroxy-5β,14β-card-20-enolide. These are separated by further chromatography on kieselgel with a mixture of methylene chloride and ethyl acetate (5:4) as eluant. 550 mg, representing 27 % of the theoretical yield, of 3-ethyl-3β,14-dihydroxy-5β,14β-card-20-enolide having the following physical characteristics were obtained:

m.p. = 184° − 187°C (recrystallized from a methylene chloride/diethyl ether mixture),
$[\alpha]_D^{20} = +25°$ ($c = 0.5$, chloroform),
UV peak (methanol): 217 nm (17 000),
Rf-value: 0.38 [ethyl acetate/methylene chloride (3/2)],
Empirical formula: $C_{25}H_{38}O_4$ (Mol. Wt.402.6): Calculated: C,74.59%; H,9.52%. Found: C,74.6%; H,9.5%.

together with 240 mg, representing 12% of the theoretical yield, of 3-ethyl-3α,14-dihydroxy-5β,14β-card-20-enolide having the following physical characteristics:

m.p. = 240° − 244°C (recrystallized from a methylene chloride/diethyl ether mixture),
$[\alpha]_D^{20} = +25°$ ($c = 0.5$, chloroform),
UV (methanol): 217 nm (16 900),
Rf-value: 0.23 [ethyl acetate/methylene chloride (3/2)],
Empirical formula $C_{25}H_{38}O_4$ (Mol. Wt. 402.6):
Calculated: C, 74.59%; H, 9.52%. Found: C, 74.2 %; H, 9.7 %.

EXAMPLE 4

Digitoxigenone (14.9 g, 40 mMol) is reacted, in a manner analogous to that described in Example 1, with 60 ml (120 mMol) of a solution of vinyl lithium in tetrahydrofuran. The crude product (18.5 g) is subjected to chromatography on kieselgel. By using a 5:4 mixture of methylene chloride and ethyl acetate as eluant and subsequently re-crystallizing the pure fractions, there are obtained 3.1 g (representing 19 % of the theoretical yield) of 3β,14-dihydroxy-3-vinyl-5β,14β-card-20-enolide having the following physical characteristics:

m.p. = 200° − 203°C (recrystallized from a methylene chloride/diethyl ether mixture),
$[\alpha]_D^{20} = +37°$ ($c = 0.5$, chloroform),
UV peak (methanol): 217 nm (16 400),
Rf-value: 0.41 [ethyl acetate/methylene chloride (3/2)],
Empirical formula: $C_{25}H_{36}O_4$ (Mol. Wt. 400.5): Calculated: C, 74.96%; H 9.06%. Found: C, 75.0 %; H 9.0 %.

1.5 g of unreacted digitoxigenone and 4.4 g (representing 22% of the theoretical yield) of pure 3β,14-dihydroxy-3-vinyl-5β,14β-card-20-enolide having the following physical characteristics:

m.p. = 210° − 214°C (recrystallized from a methylene chloride/diethyl ether mixture),
$[\alpha]_D^{20} = +34°$ ($c = 0.5$, chloroform),
UV peak (methanol): 217 nm (16,800),
Rf-value: 0.23 (ethyl acetate/methylene chloride (3/2)],
Empirical formula: $C_{25}H_{36}O_4$ (Mol. Wt. 400.5): Calculated: C, 74.96 %, H, 9.06 %. Found: C, 74.8 %; H, 9.0 %.

EXAMPLE 5

7 ml of a 0.1 molar solution of osmium tetroxide in diethyl ether and 0.47 g (1.5 mMol) of finely powdered barium chlorate monohydrate are added to a solution of 3β,14-dihydroxy-3-vinyl-5β,14β-card-20-enolide (1.1 g, 2.75 mMol, prepared as in Example 4) in 40 ml of a tetrahydrofuran/water/pyridine mixture in the ratio of 30/10/1, respectively. The reaction mixture is stirred at room temperature.

After 48 hours, a further 3.5 ml (0.35 mMol) osmium tetroxide in diethyl ether are added to the mixture. The reaction is terminated after a total of 64 hours by the addition of 1 g sodium sulfite in 10 ml pyridine/water in a 1:1 ratio and is stirred for six hours at room temperature until the cyclic osmates formed as intermediate compounds are completely disintegrated. The reaction mixture is taken up in chloroform (800 ml) and water (100 ml). The organic phase is washed with a 10 % aqueous potassium hydrogen sulfate solution (100 ml), water (100 ml) saturated aqueous sodium bicarbonate solution (100 ml) and water (2 × 100 ml), dried over sodium sulfate and evaporated.

The residue is purified by chromatography on kieselgel using a methylene chloride/acetone (5/1) mixture as eluant. The separation is continued by thin layer chromatography of the individual fractions, the identical fractions obtained by this thin layer chromatography being combined and evaporated. After recrystallization of the corresponding fractions from a methanol/diethyl ether mixture, there are obtained 430 mg, representing 36 % of the theoretical yield, of 3β,14-dihydroxy-3-(1',2'-dihydroxy ethyl)-5β,14β-card-20-enolide having the following physical characteristics:

m.p. = 242° − 255°C
$[\alpha]_D^{20} = +19.2°$ ($c = 0.25$, methanol),
UV peak (methanol): 217 nm (16 000),
Empirical formula: $C_{25}H_{38}O_6$ (Molecular weight 434.5): Calculated: C, 69.09 %; H, 8.81 %. Found: C, 68.9 %; H, 8.8 %.

EXAMPLE 6

In a manner analogous to that described in Example 5, using 3α,14-dihydroxy-3-vinyl-5β,14β-card-20-enolide (2.1 g, 5.25 mMol, obtained as described in Example 4), there are obtained 620 mg (27 % of the theoretical yield) of 3α,14-dihydroxy-3-(1',2'-dihydroxyethyl)-5β,14β-card-20-enolide.

This compound has the following physical characteristics: m.p. = 197° − 214°C (recrystallized from a methanol/diethyl ether mixture),
$[\alpha]_D^{20} = +17.4°$ ($c = 0.5$, methanol),
UV peak (methanol): 217 nm (16 500),
Rf-value: 0.35 [chloroform/methanol (5/1)],
Empirical formula: $C_{25}H_{38}O_6$ (Mol. Wt. 434.5). Calculated: C, 69.09 %; H, 8.81 %. Found: C, 69.1 %; H, 8.7 %.

EXAMPLE 7

2.0 g potassium hydrogen carbonate, 3 ml acetonitrile and 4.5 ml hydrogen peroxide (30 %) in 20 ml methanol are added to a solution of 3β,14-dihydroxy-3-vinyl-5β,14β-card-20-enolide (0.8 g, 2 mMol, described in Example 4). The reaction mixture is stirred at room temperature and the progress of the reaction is followed by thin layer chromatography using a methylene chloride/ethyl acetate (2/3) mixture as eluant. After 24 hours, a further 3 ml acetonitrile and 4.5 ml hydrogen peroxide (30 %) are added to the reaction mixture and the reaction is continued for an additional 24 hours.

The reaction mixture is then taken up in chloroform (500 ml) and water (50 ml), the organic phase is washed in water (2 × 50 ml), dried over sodium sulfate and evaporated.

The residue is subjected to chromatography on a kieselgel column using a methylene chloride/acetone (5/1) mixture as eluant. The fractions which contain the required product are combined, evaporated, and the residue is recrystallized from a methylene chloride/diethyl ether mixture. 420 mg (50 % of the theoretical yield) of 3β,14-dihydroxy-3-(oxiranyl)-5β,14β-card-20-enolide are obtained, having the following physical characteristics:

m.p. = 204° − 206°C
$[\alpha]_D^{20} = +27.5°$ ($c = 0.5$, chloroform),
UV peak (methanol): 217 nm (15,000),
Rf-value: 0.29 [methylene chloride/ethyl acetate (1/3)],
Empirical formula: $C_{25}H_{36}O_5$ (Mol. Wt. 416.5): Calculated: C, 72.08 %, H, 8.71 %. Found: C, 71.7 %; H, 8.7 %.

EXAMPLE 8

3α,14-dihydroxy-3-vinyl-5β,14β-card-20-enolide (0.9 g, 2.25 mMol, prepared as in Example 4) is dissolved in 40 ml of a 3:1 methanol/tetrahydrofuran mixture and reacted as described in Example 7. 370 mg (40 % of the theoretical yield) of 3α,14-dihydroxy-3-(oxiranyl)-5β,14β-card-20-enolide are obtained, which has the following physical characteristics:

m.p. = 221° − 228°C (recrystallized from a methylene chloride/diethyl ether mixture),
$[\alpha]_D^{20} = +18.5°$ ($c = 0.5$, chloroform),
UV peak (methanol): 217 nm (16,250),
Rf-value: 0.25 [methylene chloride/ethyl acetate (1/3)],
Empirical formula: $C_{25}H_{36}O_5$ (Mol. Wt. 416.5): Calculated: C, 72.08 %; H, 8.71 %. Found: C, 72.8 %; H, 8.8 %.

EXAMPLE 9

450 ml of an approximately 0.4 molar solution of allyl lithium in a 2:1 mixture of tetrahydrofuran/diethyl ether, prepared according to the method of J. J. Eisch et al., J. Org. Chem. 28, 2145 (1963) are added to a stirred solution of digitoxigenone (11.2 g, 30 mMol) in absolute tetrahydrofuran (200 ml) at a temperature of between −60° and −70°C. in an inert gas atmosphere. Working up is effected after four hours as described in Example 1. The raw product is subjected to chromatography on kieselgel. Elution with methylene chloride/acetone (7/1) produces two fractions. The first fraction contains a mixture of 3-allyl-3β,14-dihydroxy-5β,14β-card-20-enolide and unreacted digitoxigenone. Re-chromatography of this fraction using an ethyl acetate/acetone (8/1) eluant and subsequent recrystallization of the pure fractions yields: Fraction A - 3.2 g (26 % of the theoretical yield) of pure 3-allyl-3β,14-dihydroxy-5β,14β-card-20-enolide having the following physical characteristics:- m.p. = 164° − 165°C. (recrystallized from a mixture of methylethylketone/heptane)
$[\alpha]_D^{20} = +27°$ ($c = 0.5$, chloroform),
UV peak (methanol): 127 nm (16 000), Rf-value: 0.42 [ethyl acetate/methylene chloride (3/2)], Empirical formula: $C_{26}H_{38}O_4$ (Mol. Wt. 414.6): Calculated: C, 75.32 %; H, 9.24 %. Found: C, 75.5 %; H, 9.3 %.

1.2 g unreacted digitoxigenone, and Fraction B, after recrystallization from a methylene chloride/diethyl ether mixture, 4.0 g (32 % of the theoretical yield) of 3-allyl-3α,14-dihydroxy-5β,14β-card-20-enolide having the following physical characteristics:

m.p. = 226° – 232°C $[\alpha]_D^{20} = + 32°$ ($C = 0.5$, chloroform),

UV peak (methanol): 217 nm (17 000),

Rf-value: 0.25 [ethyl acetate/methylene chloride (3/2)],

Empirical formula: $C_{26}H_{38}O_4$ (Mol. Wt. 414.6): Calculated: C, 75.32 %; H, 9.24 %. Found: C, 75.2 %; H, 9.2 %.

EXAMPLE 10

10 ml of a molar solution of osmium tetroxide in diethyl ether and 0.81 g (2.5 mMol) of finely powdered barium chlorate monohydrate are added to a solution of 3-allyl-3β,14-dihydroxy-5β,14β-card-20-enolide (1.7 g, 4.1 mMol, prepared as in Example 9) in 40 ml of a mixture of tetrahydrofuran, water and pyridine (30/10/1). The reaction mixture is stirred at room temperature.

After 24 hours, a further 10 ml of a 0.1 molar osmium tetroxide solution are added to the reaction mixture. After a total reaction time of 70 hours, the reaction is terminated by the addition of 2.0 g sodium sulfate and 25 ml of a 1:1 mixture of pyridine and water. The products are then further worked up as described in Example 5.

Chromatography on kieselgel with a mixture of methylene chloride and ethyl acetate as eluant followed by crystallization of the pure fractions yields 650 mg (35% of the theoretical yield) of 3β,14-dihydroxy-3-(2',3'-dihydroxypropyl)-5β,14βcard-20-enolide having the following physical characteristics:

m.p. = 238° - 242°C $[\alpha]_D^{20} = + 19.5°$ ($c = 0.4$, methanol),

UV peak (methanol): 217 nm (16,800),

Rf-value: 0.39 [chloroform/methanol (5/1)],

Empirical formula: $C_{26}H_{40}O_6$ (Mol. Wt. 448.6): Calculated: C, 69.61 %; H, 8.99 %. Found: C, 69.4 %; H, 8.9 %.

EXAMPLE 11

In a manner analogous to that described in Example 10, 3-allyl-3α,14-dihydroxy-5β,14β-card-20-enolide (1.04 g, 2.5 mMol, prepared as in Example 9) is used as a starting material. After chromatography of the crude product on kieselgel using a methylene chloride/methanol mixture (20/1) as eluant and crystallization of the pure fractions from a methylene chloride/diethyl ether/hexane mixture, 481 mg (48 % of the theoretical yield) of 3α, 14-dihydroxy-3-(2',3'-dihydroxypropyl)-5β,14β-card-20-enolide is obtained, having the following physical characteristic:

m.p. = 210° – 225°C, $[\alpha]_D^{20} = + 17.8°$ ($c = 0.5$, methanol),

UV peak (methanol): 217 nm (16 400),

Rf-value: 0.39 [chloroform/methanol (5/1)],

Empirical formula: $C_{26}H_{40}O_6$ (Mol. Wt. 448.6): Calculated: C, 69.61 %; H, 8.99 %. Found: C, 68.6 %; H 9.1 %.

EXAMPLE 12

3.0 g potassium bicarbonate, 5 ml acetonitrile and 8 ml hydrogen peroxide (30 %) are added to a solution of 3-allyl-3β,14-dihydroxy-5β,14β-card-20-enolide (1.4 g, 3.35 mMol, prepared as in Example 9) in 20 ml methanol. The reaction mixture is stirred at room temperature, the progress of the reaction being followed by thin layer chromatography using a 2:3 mixture of methylene chloride and ethyl acetate.

After four hours, a further 5 ml acetonitrile and 8 ml hydrogen peroxide (30%) are added. The reaction is virtually complete after 16 hours. The reaction mixture is taken up in chloroform (500 ml) and water (50 ml). The organic phase is washed with water (2 × 50 ml), dried over sodium sulfate and evaporated.

Chromatography of the residue on kieselgel using a methylene chloride/acetone (8/1) mixture as eluant followed by recrystallization from a methylene chloride/diethyl ether mixture yields 490 mg (34% of the theoretical yield) of 3β,14-dihydroxy-3-(2',3'-epoxypropyl)-5β,14β-card-20-enolide, having the following physical characteristics:

m.p. = 153° – 155°C, $[\alpha]_D^{20} = + 16°$ ($c = 0.5$, chloroform)

UV peak (methanol): 218 nm (16 000),

Rf-value: 0.24 [methylene chloride/ethyl acetate (1/3)],

Empirical formula: $C_{26}H_{38}O_5$ (Mol. Wt. 430.6): Calculated: C, 72.53%; H, 8.98%. Found: C, 72.0%; H, 8.9%.

EXAMPLE 13

3-allyl-3α,14-dihydroxy-5β,14β-card-20-enolide (1.8 g, 4.35 mMol, prepared as in Example 9) is dissolved in 80 ml of a 5:2 methanol/tetrahydrofuran mixture and reacted as described in Example 12. There are obtained 820 mg (44% of the theoretical yield) of 3α,14-dihydroxy-3-(2',3'-epoxypropyl)-5β,14β-card-20-enolide having the following physical characteristics:

m.p. = 193° – 198°C (recrystallized from a mixture of methylene chloride and diethyl ether), $[\alpha]_D^{20} = + 24°$ ($c = 0.5$, chloroform), UV peak (methanol): 218 nm (16 000), Rf-value: 0.17 [methylene chloride/ethyl acetate (1/3)], Empirical formula: $C_{26}H_{38}O_5$ (Mol. Wt. 430.6): Calculated: C, 72.55%; H, 8.98%. Found: C, 72.7%; H, 9.0%.

EXAMPLE 14

A suspension of 2.4 g (100 mMol) sodium hydride in 100 ml absolute dimethyl sulfoxide is stirred, under nitrogen, for 45 minutes at a temperature of between 60° and 65°C. The mixture is cooled to 0°C. and mixed with 250 ml dimethylsulfoxide, which has previously been saturated at 0°C with acetylene. After 30 minutes at 0°C, a solution of digitoxigenone (7.4 g, 20 mMol) is added to the solution of sodium acetylide thus produced. The temperature of the reaction mixture is allowed to rise to room temperature and the reaction is continued by introducing acetylene into the reaction mixture in an atmosphere of nitrogen and acetylene atmosphere. This is continued for 24 hours.

The reaction is terminated by the addition of 200 ml of a saturated aqueous solution of ammonium chloride. After the addition of chloroform (2,000 ml), the organic phase is washed with a saturated aqueous sodium bicarbonate solution and then repeatedly with water. The organic phase is then dried over sodium sulfate and evaporated. The crude product (11 g) is separated by chromatography on kieselgel. By using a 40:1 chloroform/methanol mixture as eluant, the first fraction obtained consists of 0.5 digitoxigenone. Further chromatography of the digitoxigenone-free fractions with a 5:4 mixture of methylene chloride and ethyl acetate as eluant followed by recrystallization of the pure fractions yields 450 mg. (5.7% of the theoretical yield) of 3-ethinyl-3β,14-dihydroxy-5β,14β-card-20-enolide having the following physical characteristics:

m.p. = 223 - 228°C. (recrystallized from a methylene chloride/hexane mixture), $[\alpha]_D^{20} = + 27.9°$ ($c = 0.5$, chloroform), UV peak (methanol): 217 nm (16.000), Rf-value: 0.42 [ethyl acetate/methylene chloride (3/2)], Empirical formula: $C_{25}H_{34}O_4$ (Mol. Wt. 398.5) Calculated: C, 75.34%; H, 8.60%. Found: C, 75.2%; H, 8.7%.

There are also obtained 5.1 g (64% of the theoretical yield) 3-ethinyl-3α,14-dihydroxy-3β, 14β-card-20-enolide having the following physical characteristics:

m.p. = 215° - 221°C (recrystallized from methylene chloride/hexane), $[\alpha]_D^{20} = + 26.5°C$ ($c = 0.5$, chloroform), UV peak (methanol): 217 nm (15 900), Rf-value: 0.31 [ethyl acetate/methylene chloride (3/2)], Empirical formula: $C_{25}H_{34}O_4$ (Mol. Wt. 398.5): Calculated: C, 75.34%; H, 8.60%. Found: C, 75.5%; H, 8.5%.

EXAMPLE 15

Digitoxigenone (5.8 g, 15 mMol) is dissolved in 150 ml absolute tetrahydrofuran and, in a manner analogous to that described in Example 1, is reacted with 40 ml of a 2 molar solution of phenyl lithium in a 7:3 mixture of benzene and diethyl ether.

The reaction product is subjected to chromatography on kieselgel, using an 8:1 mixture of methylene chloride and acetone as eluant. After recrystallization of the pure fractions, there are obtained 1.3 g (19% of the theoretical yield) of 3β,14-dihydroxy-3-phenyl-5β,14β-card-20-enolide, having the following physical characteristics:

m.p. = 178° – 184°C (recrystallized from a mixture of methylethylketone and heptane)

$[\alpha]_D^{20} = + 41°$ ($c = 0.5$, chloroform),

UV peak (methanol): 213 nm (24 800),

Rf-value: 0.44 [ethyl acetate/methylene chloride (3/2)],

Empirical formula: $C_{29}H_{38}O_4$ (Mol. Wt. 450.59) Calculated: C, 77.30%; H, 8.50%. Found: C, 77.0%; H, 8.8%.

and 1.7 g (25% of the theoretical yield) of 3α,14-dihydroxy-3-phenyl-5β,14β-card-20-enolide having the following physical characteristics:

m.p. = 215° – 224°C (recrystallized from acetone/diethyl ether), $[\alpha]_D^{20} = + 41°$ ($c = 0.5$, chloroform), UV peak (methanol): 212 nm (24 700), Rf-value: 0.30 [ethyl acetate/methylene chloride (3/2)], Empirical formula: $C_{29}H_{38}O_4$ (Mol. Wt. 450.6): Calculated: C, 75.30%; H, 8.50%. Found: C, 75.2%; H, 8.6%.

EXAMPLE 16

A solution of 2.7 g (7 mMol) 12β,14-dihydroxy-3-oxo-5β, 14β-card-20-enolide (3-dehydrodigoxigenine) in 160 ml absolute tetrahydrofuran is reacted, in a manner analogous to that described in Example 1, with 21 ml (42 mMol) of a solution of methyl lithium in diethyl ether. Chromatography of the crude product on kieselgel using an 8:1 mixture of ethyl acetate and acetone (8/1) as eluant followed by recrystallization of the pure fractions produces 1.6 g (57% of the theoretical yield) of 3β,12β,14-trihydroxy-3-methyl-5β,14β-card-20-enolide:

m.p. = 195° – 204°C (recrystallized from methylene chloride/diethyl ether), $[\alpha]_D^{20} = + 25.1°$ ($c = 0.5$, chloroform), UV peak (methanol): 217 nm (17 400), Rf-value: 0.13 [ethyl acetate/methylene chloride (3/2)], Empirical formula: $C_{24}H_{36}O_5$ (Mol. Wt. 404.5): Calculated: C, 71.23%; H, 8.97%. Found: C, 70.9%; H, 9.0%.

and 311 mg (11% of the theoretical yield) of 3α,12β,14-trihydroxy-3-methyl-5β,14β-card-20-enolide having the following physical characteristics:

m.p. = 248° – 260°C (recrystallized from acetone/diethyl ether), $[\alpha]_D^{20} = + 25.4°$ [$c = 0.5$, chloroform/ethanol (10/1)], UV peak (methanol): 217 nm (15 800), Rf-value: 0.05 [ethyl acetate/methylene chloride (3/2)], Empirical formula: $C_{24}H_{36}O_5$ (Mol. Wt. 404.5): Calculated: C, 71.25%; H, 8.97%. Found: C, 71.3%; H, 9.21%.

What is claimed is:

1. Compound of the formula

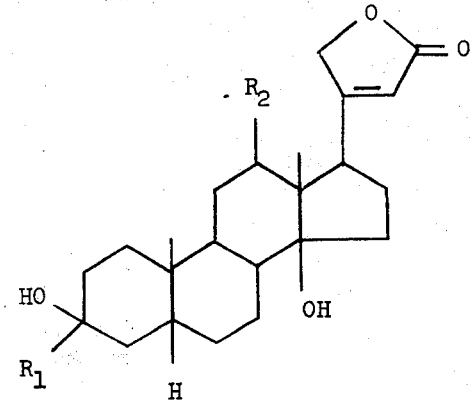

in which $R_1$ is alkyl of 1 to 4 carbon atoms, vicinal epoxy- or dihydroxyalkyl of 2 to 4 carbon atoms, alkenyl or alkinyl of 2 to 4 carbon atoms, or phenyl and $R_2$ is H or OH.

2. A compound as defined in claim 1 in which $R_1$ is methyl, ethyl, oxiranyl, 2',3'-epoxypropyl, 1',2'-dihydroxyethyl, 2',3'-dihydroxypropyl, vinyl, allyl, ethinyl or phenyl.

3. The compound defined in claim 1 which is 3α,14-dihydroxy-3-methyl-5β,14β-card-20-enolide.

4. The compound defined in claim 1 which is 3β,14-dihydroxy-3-methyl-5β,14β-card-20-enolide.

5. The compound defined in claim 1 which is 3-ethyl-3α,14-dihydroxy-5β,14β-card-20-enolide.

6. The compound defined in claim 1 which is 3-ethyl-3β,14-dihydroxy-5β,14β-card-20-enolide.

7. The compound defined in claim 1 which is 3α,14-dihydroxy-3-vinyl-5β,14β-card-20-enolide.

8. The compound defined in claim 1 which is 3β,14-dihydroxy-3-vinyl-5β,14β-card-20-enolide.

9. The compound defined in claim 1 which is 3-allyl-3α,14-dihydroxy-5β,14β-card-20-enolide.

10. The compound defined in claim 1 which is 3-allyl-3β,14-dihydroxy-5β,14β-card-20-enolide.

11. The compound defined in claim 1 which is 3-ethinyl-3α,14-dihydroxy-5β,14β-card-20-enolide.

12. The compound defined in claim 1 which is 3-ethinyl-3β, 14-dihydroxy-5β,14β-card-20-enolide.

13. The compound defined in claim 1 which is 3α,14-dihydroxy-3-phenyl-5β,14β-card-20-enolide.

14. The compound defined in claim 1 which is 3β,14-dihydroxy-3-phenyl-5β,14β-card-20-enolide.

15. The compound defined in claim 1 which is 3α,12β,14-trihydroxy-3-methyl-5β,14β-card-20-enolide.

16. The compound defined in claim 1 which is 3β,12β, 14-trihydroxy-3-methyl-5β,14β-card-20-enolide.

17. The compound defined in claim 1 which is 3β,14-dihydroxy-3-(1',2'-dihydroxyethyl)-5β,14β-card-20-enolide.

18. The compound defined in claim 1 which is 3α,14-dihydroxy-3-(1',2'-dihydroxyethyl)-5β,14β-card-20-enolide.

19. The compound defined in claim 1 which is 3β,14-dihydroxy-3-(2',3'-dihydroxypropyl)-5β,14β-card-20-enolide.

20. The compound defined in claim 1 which is 3α,14-dihydroxy-3-(2',3'-dihydroxypropyl)-5β,14β-card-20-enolide.

21. The compound defined in claim 1 which is 3β,14-dihydroxy-3-(oxiranyl)-5β,14β-card-20-enolide.

22. The compound defined in claim 1 which is 3α,14-dihydroxy-3-(oxiranyl)-5β,14β-card-20-enolide.

23. The compound defined in claim 1 which is 3β,14-dihydroxy-3-(2',3'-epoxypropyl)-5β,14β-card-20-enolide.

24. The compound defined in claim 1 which is 3α,14-dihydroxy-3-(2',3'-epoxypropyl)-5β,14β-card-20-enolide.

25. A process for making a compound of the formula

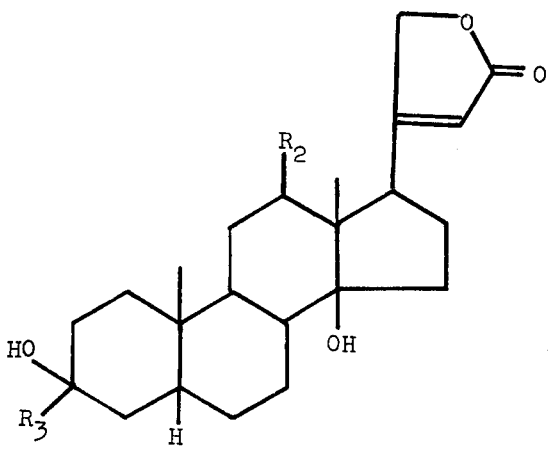

wherein $R_2$ is H or OH and $R_3$ is alkyl of 1 to 4 carbon atoms, alkenyl or alkinyl of 2 to 4 carbon atoms, or phenyl, which comprises reacting a compound of the formula

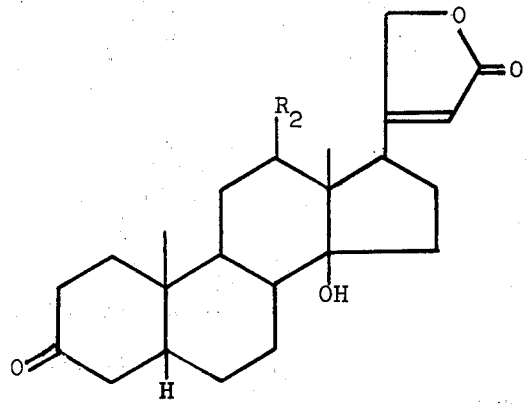

with an organo-metallic compound of the formula $R_3$ — Me or $R_3MgX$, wherein Me is lithium, sodium, or potassium and X is chlorine, bromine, or iodine.

26. A process as defined in claim 25 wherein $R_3$ is alkenyl and wherein the 3-alkenyl compound prepared is subsequently hydroxylated with osmium tetroxide and barium chlorate or is subsequently epoxylated with hydrogen peroxide and acetonitrile in the presence of potassium hydrogen carbonate.

27. A process as defined in claim 26 wherein the reaction conditions for the hydroxylation or epoxylation step are substantially neutral.

28. A process as defined in claim 25 wherein the reaction is carried out in the presence of an inert solvent.

29. A process as defined in claim 28 wherein the solvent is absolute tetrahydrofuran.

30. A process as defined in claim 25 wherein the organo-metallic compound is used in excess.

31. A process as defined in claim 30 wherein the organo-metallic compound is present in a 2 to 6-fold excess.

32. A process as defined in claim 25 wherein the reaction is carried out in the absence of atmospheric oxygen.

33. A process as defined in claim 25 wherein the reaction temperature is between −70° and +20°C.

34. A process as defined in claim 25 wherein the reaction time is between 4 and 24 hours.

35. A process as defined in claim 25 wherein the crude product obtained is purified by chromatography and re-crystallization.

36. A method of treatment which comprises orally administering to a cardiac patient from 0.01 to 0.2 mg/kg of body weight of a compound as defined in claim 1.

* * * * *